(12) United States Patent
Pitts et al.

(10) Patent No.: US 7,560,409 B2
(45) Date of Patent: Jul. 14, 2009

(54) PHOTO-OXIDATION CATALYSTS

(75) Inventors: J. Roland Pitts, Lakewood, CO (US); Ping Liu, Irvine, CA (US); R. Davis Smith, Golden, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 170 days.

(21) Appl. No.: 11/207,844

(22) Filed: Aug. 19, 2005

(65) Prior Publication Data

US 2007/0042906 A1    Feb. 22, 2007

(51) Int. Cl.
| | |
|---|---|
| B01J 27/132 | (2006.01) |
| B01J 23/00 | (2006.01) |
| B01J 23/42 | (2006.01) |
| B01J 23/44 | (2006.01) |
| B01J 8/00 | (2006.01) |
| B01D 53/56 | (2006.01) |
| B01D 53/86 | (2006.01) |
| B01D 53/52 | (2006.01) |
| C01B 21/00 | (2006.01) |
| C01B 17/00 | (2006.01) |
| C01B 17/48 | (2006.01) |
| C01B 17/16 | (2006.01) |
| C01B 31/18 | (2006.01) |
| C01B 31/24 | (2006.01) |
| G01N 30/96 | (2006.01) |
| G01N 17/00 | (2006.01) |

(52) U.S. Cl. ............. 502/228; 502/325; 502/339; 502/350; 423/239.1; 423/242.1; 423/244.01; 423/418.2; 423/511; 423/539; 423/563; 422/88; 422/91

(58) Field of Classification Search ............... 502/228, 502/325, 339, 350; 423/239.1, 242.1, 244.01, 423/416.2, 418.2, 511, 539, 563; 422/88, 422/91
See application file for complete search history.

(56) References Cited

U.S. PATENT DOCUMENTS

| 4,028,250 | A | | 6/1977 | Loft | |
|---|---|---|---|---|---|
| 4,373,375 | A | | 2/1983 | Terhume et al. | |
| 4,661,320 | A | * | 4/1987 | Ito et al. ............... | 422/86 |
| 4,892,712 | A | * | 1/1990 | Robertson et al. ......... | 422/186 |
| 5,194,161 | A | * | 3/1993 | Heller et al. ............ | 210/748 |
| 5,367,283 | A | * | 11/1994 | Lauf et al. ............ | 338/34 |

(Continued)

FOREIGN PATENT DOCUMENTS

EP     1 291 331    *   3/2003

OTHER PUBLICATIONS

"Titanium (IV) Oxide Photocatalysts with Palladium", J. Papp et al. Chem. Mater. 1993, 5, pp. 284-288.*

(Continued)

*Primary Examiner*—Patricia L Hailey
(74) *Attorney, Agent, or Firm*—Paul J. White (57) ABSTRACT

Photo-oxidation catalysts and methods for cleaning a metal-based catalyst are disclosed. An exemplary catalyst system implementing a photo-oxidation catalyst may comprise a metal-based catalyst, and a photo-oxidation catalyst for cleaning the metal-based catalyst in the presence of light. The exposure to light enables the photo-oxidation catalyst to substantially oxidize absorbed contaminants and reduce accumulation of the contaminants on the metal-based catalyst. Applications are also disclosed.

36 Claims, 5 Drawing Sheets

U.S. PATENT DOCUMENTS

| | | | |
|---|---|---|---|
| 5,451,920 A * | 9/1995 | Hoffheins et al. ............. 338/34 |
| 5,527,755 A | 6/1996 | Wenski et al. |
| 5,693,302 A | 12/1997 | Gary |
| 5,708,735 A | 1/1998 | Benson et al. |
| 5,778,664 A | 7/1998 | Janata et al. |
| 5,779,912 A * | 7/1998 | Gonzalez-Martin et al. . 210/748 |
| 5,779,980 A | 7/1998 | Hatfield |
| 5,919,422 A | 7/1999 | Yamanaka et al. |
| 5,942,676 A | 8/1999 | Potthast et al. |
| 6,006,582 A | 12/1999 | Bhandari et al. |
| 6,029,500 A | 2/2000 | Tom |
| 6,070,450 A | 6/2000 | Takao et al. |
| 6,103,363 A | 8/2000 | Boire et al. |
| 6,159,421 A | 12/2000 | Fujii |
| 6,263,723 B1 | 7/2001 | Takao et al. |
| 6,326,079 B1 * | 12/2001 | Philippe et al. ............. 428/325 |
| 6,407,033 B1 * | 6/2002 | Kimura et al. ............. 502/350 |
| 6,535,658 B1 * | 3/2003 | Mendoza et al. ............. 385/12 |
| 6,634,213 B1 * | 10/2003 | O'Connor et al. .......... 73/31.06 |
| 6,723,566 B2 * | 4/2004 | Lee et al. .................... 436/144 |
| 7,011,737 B2 * | 3/2006 | Varghese et al. ............ 205/189 |
| 2005/0103639 A1 * | 5/2005 | Lu et al. ..................... 205/322 |

OTHER PUBLICATIONS

"Photooxidative self-cleaning transparent titanium dioxide films on glass", Y. Paz et al. J. Mater. Res., vol. 10, No. 11, Nov. 1995, pp. 2842-2848.*

English translation of EP 1 291 331 provided by Examiner.*

Yong-su Oh et al., "Preparation and characterization of an optically-detectable hydrogen gas sensor consisting of Pd/WO3 thin films," Sensors and Actuators B, 13-14 (1993) pp. 547-548.

Zorn, Michael E. et al., "Catalytic and Photocatalytic Oxidation of Ethylene on Titania-Based Thin-Films," Environ. Sci. Technol. 2000 34, pp. 5206-5210.

Williamson, W.G. et al., "Palladium and Platinum/Rhodium Dual-Catalyst NLEV and Tier IIa Close-Coupled Emission Solutions," SAE Technical Paper Series 2001-01-0923.

* cited by examiner

PHOTO-OXIDATION CATALYSTS

CONTRACTUAL ORIGIN

The United States Government has rights in this invention under Contract No. DEAC36-99GO10337 between the United States Department of Energy and the National Renewable Energy Laboratory, a Division of the Midwest Research Institute.

TECHNICAL FIELD

The described subject matter relates to catalysts, and more specifically, to photo-oxidation catalysts.

BACKGROUND

Hydrogen fuel is used in a wide variety of commercial applications, such as, e.g., transportation, chemical production, and refineries, to name only a few examples. Due to the explosive nature of hydrogen gas, there is a need to detect hydrogen gas leaks economically, safely and reliably.

Several types of hydrogen sensors are available, including hydrogen field-effect transistor (FET) sensors, thin film and thick film metallic sensors, and fiber-optic sensors. These sensors typically employ a palladium film as a catalyst. Molecular hydrogen coming into contact with the palladium dissociates on the surface, and atomic hydrogen diffuses through the film. Physical or optical changes in or adjacent to the film are used to detect the presence of hydrogen. For example, the light being transmitted in an optical sensor decreases in response to the presence of hydrogen. The change in transmittance corresponds to the amount of hydrogen that is present.

These hydrogen sensors need to respond quickly to the presence of hydrogen, e.g., well before an explosive limit of four percent in air is reached, so that there is sufficient time for corrective action or evacuation. However, some sensors have thin films that are not sufficiently stable upon cyclic exposures to hydrogen. Some sensors have thin films that undesirably foul due to impurities and pollutants when they react with air. Some sensors have thick films or thin films that are unstable with repeated exposure to hydrogen, or excessive concentrations of hydrogen. Some sensors have palladium films that foul due to impurities and pollutants in the air, such as, e.g., hydrocarbons, carbon monoxide, and sulfur bearing substances.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

An exemplary catalyst system may comprise a metal-based catalyst and a photo-oxidation catalyst for cleaning the metal-based catalyst in the presence of light. The exposure to light enables the photo-oxidation catalyst to substantially oxidize absorbed contaminants and reduce accumulation of contaminants on the metal-based catalyst.

An exemplary hydrogen sensor may comprise a composite of thin films. The composite of thin films includes: a coating of titanium dioxide defining a top thin film; a catalytic layer of palladium defining an intermediate thin film; and a chemochromic layer of tungsten oxide defining a bottom thin film. A glass substrate supports the composite of thin films. A light source probes the composite of thin films with light to facilitate a reaction with the ambient air and water vapor therein, causing photo-oxidation of contaminants on the composite of thin films.

An exemplary method for cleaning a metal-based catalyst may comprise: providing a photo-oxidation catalyst on or adjacent to the metal-based catalyst, and exposing the photo-oxidation catalyst to light to oxidize absorbed contaminants on the metal-based catalyst.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

DETAILED DESCRIPTION

Briefly, the systems and methods described herein prevent or substantially reduce the effect of pollutants and contaminants (e.g., in ambient air and industrial environments) on metal-based catalysts, such as palladium (Pd) or other noble or semi-noble metals. In an exemplary embodiment, a photo-oxidation catalyst, such as, e.g., titanium dioxide (titania), may be exposed to ultraviolet (UV) or visible light to clean the metal-based catalyst. Accordingly, the systems and methods may be implemented to increase performance, lifetime, and reliability of the metal-based catalyst.

Exemplary systems and methods may be better understood with reference to the Figures and following discussion.

Figure 1:
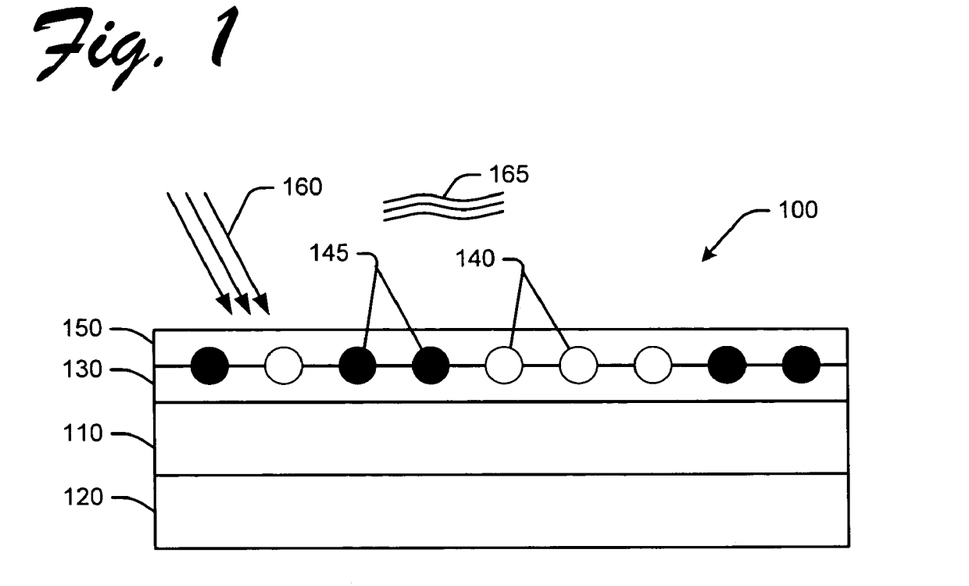
FIG. 1 is a high-level diagram of an exemplary catalyst system.

FIG. 1 is a high-level diagram of an exemplary catalyst system 100. For purposes of illustration, the catalyst system 100 may be an optical hydrogen sensor, although other catalyst systems are also contemplated as will be readily appreciated after becoming familiar with the teachings herein. Catalyst system 100 may include a primary reactive or indicator layer 110, such as a metal oxide that changes color when it reacts with atomic hydrogen. The primary layer 110 may reside on or be otherwise bound to a support substrate 120. For example, the primary layer 110 may be applied to the substrate 120 as a thick film, a thin continuous film, or have an "island" configuration, where the film is not completely continuous on the substrate 120. Optionally, a catalytic over-layer 130 may be provided over the primary layer 110. The catalytic over-layer 130 acts as a dissociation catalyst, e.g., forming atomic hydrogen which subsequently reacts with the primary layer 110.

The type of material employed as the primary layer 110 may include metal oxides (e.g., $WO_3$, $MoO_3$, $V_2O_5$, NiO) or other compounds that indicate the presence of atomic hydrogen. The substrate 120 may be a solid material, ceramic, polymer, or glass, or it may be particulate support, such as aluminum oxide powder. The over-layer 130 may be palladium or other noble or semi-noble metals such as platinum group metals and their alloys. Platinum group metals are Pt, Pd, Rh, Ir, Ru. And Os, while alloys with such metals as Fe, Co, Ni, and Cu, for example, represent functional catalytic alloys for particular applications.

Over time, contaminants may react with the catalyst system 100, binding to the catalyst 130 and degrading its operation (e.g., the ability to detect hydrogen). Exemplary contaminants include, but are not limited to, gases in the ambient air or other process stream, such as, e.g., hydrocarbons, carbon monoxide, and hydrogen sulfide or other sulfur bearing molecules. In FIG. 1, "clean" or functional catalytic sites 140 are not shaded, and catalytic sites 145 which have absorbed pollutants are shaded.

Figure 1A:
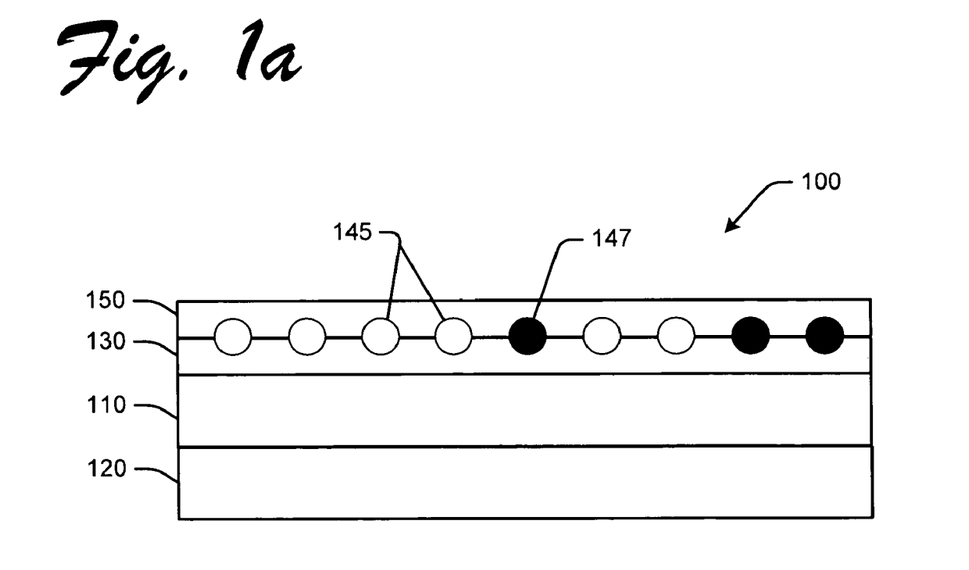
FIG. 1a illustrates cleaning of the exemplary catalyst system after exposure to light.

Accordingly, the catalyst system 100 may implement a photo-oxidation catalyst or photocatalyst 150, which in the presence of visible or ultraviolet light 160 and water vapor 165 (e.g., in the ambient air), "regenerates" or "cleans" the catalyst 130 of contaminants. FIG. 1a illustrates cleaning of the exemplary catalyst system 100 after exposure to light 160 (and water vapor 165). It is observed that at least some of the binding sites 145 which had absorbed pollutants are regenerated or "clean." Although other binding sites 147 which were previously clean may have absorbed pollutants, overall function of the catalyst system 100 is maintained by the cleaning action. With ongoing exposure to light 160, these binding sites 147 will also be regenerated or "cleaned."

The photocatalyst 150 may be applied to the surface of any catalyst 130 as a thin film or thick film of photocatalytic material, or may be a composite of fine particles adhered to the substrate 120 and surrounding the primary layer 110 (or catalyst 130). For example, a solid substrate or particles of a ceramic support, such as aluminum oxide, may be coated with islands of a platinum group metal to enhance chemical reactions at the surface. Or for example, the photocatalyst 150 may be so thin, or dispersed, in such a way as to provide only close proximity to the primary layer 110 islands. Accordingly, productive photo-oxidation of surface contaminants can still regenerate the catalyst 130.

Photocatalyst 150 may be selected such that it does not react with the primary layer 110, dissociation catalyst 130, or the substrate 120 under conditions of use. In an exemplary embodiment, the photocatalyst 150 may comprise anatase titania, rutile titania, mixtures of titania and other metal oxides, or other photocatalyst materials having substantially similar chemical and physical characteristics. For example, the photocatalyst 150 may comprise a coating fabricated from a porous, colloidal suspension of anatase titania particles. The size of exemplary particles range in size from about 15 nanometers (nm) to about 30 nm.

Exemplary particles for the photocatalyst 150 may be synthesized by a conventional hydrothermal process from an alkoxide precursor, such as, e.g., titanium isopropoxide. In an exemplary embodiment, the particles are fabricated using an aqueous acidic medium, such a, e.g., dilute nitric acid. The resultant titania suspension is diluted in a solvent such as ethanol in a particular ratio to obtain a proper consistency for coating. The coating may be applied to the catalyst system 100, e.g., by spin coating, spray coating, blading, and dip coating, to name only a few examples.

The photocatalyst 150 permits molecules in the process stream to react and form the product for which the catalyst system is designed. Light is applied to the catalyst configuration to activate the regeneration or cleaning action. The light illuminates the active surfaces of the photocatalyst 150 and may impinge on those surfaces from any direction.

In an exemplary embodiment, the light source may be a light emitting diode (LED) coupled to a fiber optic cable. It is noted, however, that any suitable light source may be provided for emitting light 160. For example, the light source may be one or more fluorescent lamps adapted to emit a beam of ultraviolet or visible light. Or the light source may be any of a wide variety of high intensity discharge lamps, such as, e.g., a mercury vapor lamp, light emitting diodes (LEDs), or even sunlight.

The light source utilizes light in the portion of the electromagnetic spectrum that activates the photocatalyst 150. The light source and its light output 160 are adapted and arranged to facilitate a reaction of the photocatalyst 150 with ambient air and water vapor. Illuminating the catalyst system 100 enables the photocatalyst 150 to produce hydroxide radicals for oxidizing contaminants 145 on the catalyst 130, as well as contaminants on the photocatalyst 150. Oxidation results in the production of stable and volatile products that are then removed by the process stream or ambient atmosphere so that they no longer interfere with the surface reactions for which the catalyst system 100 was designed.

The light source may produce collimated, uncollimated, or focused radiation. For example, uncollimated radiation may be delivered to the catalyst system 100 by locating a mercury lamp in proximity to the catalyst system 100. In another example, collimated radiation may be delivered to the catalyst system 100 with fiber-optic cables fitted with collimating lenses. Separate beams of radiation may also be used. For example, one beam may operate in a portion of the electromagnetic spectrum to optimize the detection of film (layer 110 or catalyst 130) properties, while the other, separate beam is used in the photocatalytic cleaning process to keep the catalyst system 100 operational.

During an exemplary cleaning operation, the catalyst system 100 is exposed to uncollimated ultraviolet light 160 having a wavelength in the range of about 254 nm to about 385 nm. The intensity or level of ultraviolet light actually utilized is suitable for matching a corresponding level of photo-oxidation activity of the photocatalyst 150 so as to keep sorption contaminants cleaned off the surface of the catalyst 130 without oxidizing it. The ultraviolet light beam 160 continuously probes the system 100 in ambient air and causes the particles of titania to form hydroxide radicals from water vapor in the atmosphere. The hydroxide radicals oxidize the contaminants adsorbed on an upper surface defined by the junction of the photocatalyst 150 and the catalyst 130.

Additional hydroxide radicals may migrate through the photocatalyst 150. Contaminants that make it through the photocatalyst 150 and occupy sites on the upper surface of the catalyst 130 are oxidized and converted to volatile species, which escape from photocatalyst 150 and the catalyst 130. Both physisorbed and chemisorbed species are effectively removed.

Figure 2:
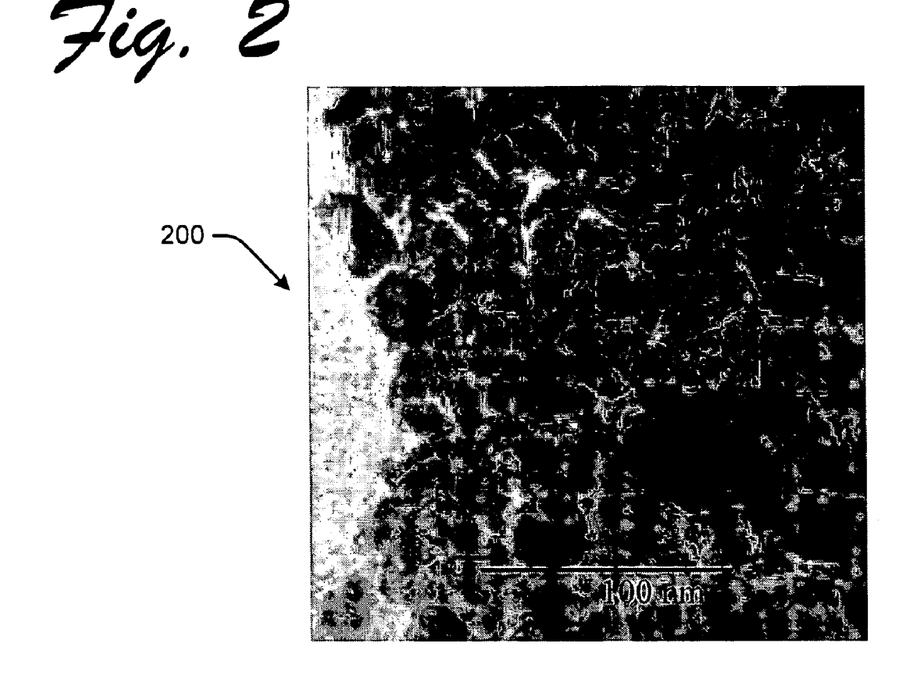
FIG. 2 is a transmission electron microscope (TEM) image of an exemplary photo-oxidation catalyst.
Figure 3:
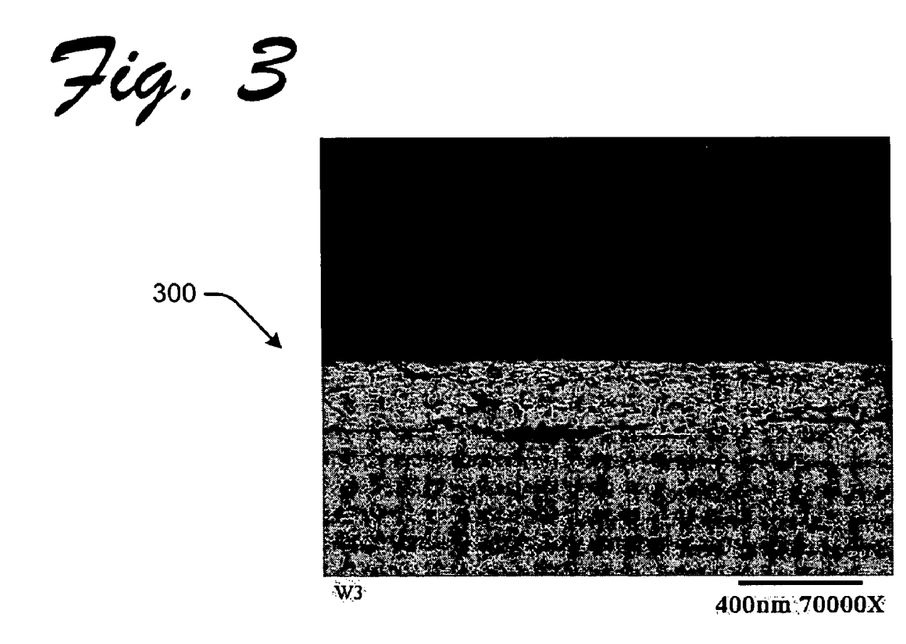
FIG. 3 is an scanning electron microscope (SEM) image of a cross section of an exemplary photo-oxidation catalyst layer on a substrate.

FIG. 2 is a TEM image 200 of an exemplary photo-oxidation catalyst. FIG. 3 is an SEM image 300 of a cross section of an exemplary photo-oxidation catalyst layer on a substrate. In this exemplary embodiment, the photo-oxidation catalyst comprises a $TiO_2$ thin film. $TiO_2$ colloids were synthesized by a hydrothermal process from titanium iso-propoxide precursor. The resulting particle size was in the range of 15-30 nm. The $TiO_2$ suspension was diluted in ethanol and spin-coated at 2000 rpm on the thin film sensor stacks. The sensors were continuously exposed to 365 nm radiation from a UV pencil lamp in ambient atmosphere. Performance was measured periodically using a diode array fiber-optic UV/VIS spectrophotometer (Ocean Optics model S2000). Laboratory experiments indicate that variations in synthesis temperature, particle size or precursor purity do not significantly alter the effectiveness of the film.

It is readily appreciated that applications of this technology may include, but are not limited to, protecting Pd or other noble metal-based catalysts used in hydrogen sensors, for hydrogen separation membranes, for maintaining functionality of metal membranes used for hydrogen dissociation in fuel cell membrane assemblies, and preventing poisoning or cleaning fouled supported catalysts used in fluidized beds for industrial catalysts. Exemplary applications are discussed in more detail below with reference to FIGS. 4-6.

EXAMPLES

Figure 4:
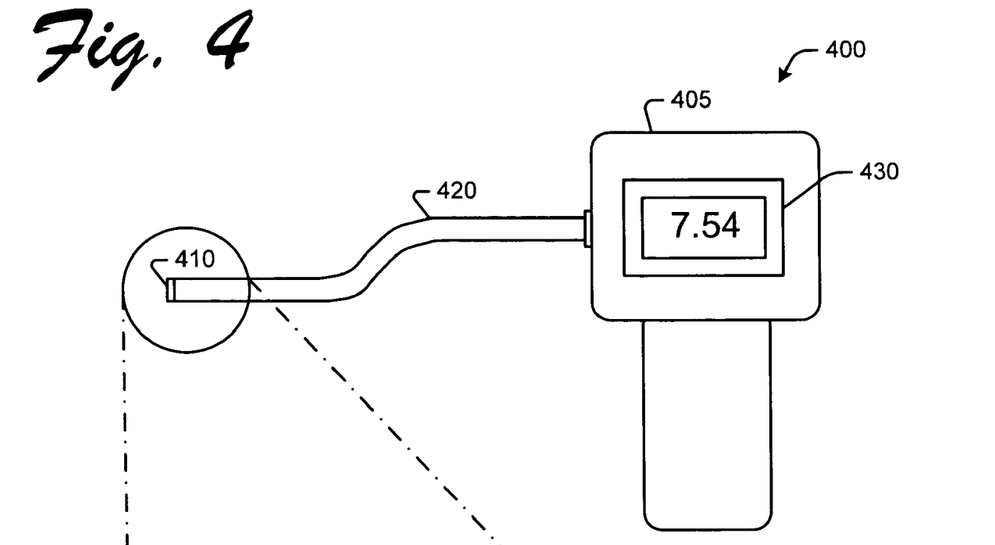
FIG. 4 is a schematic diagram of a fiber optic hydrogen sensor.

FIG. 4 is a schematic diagram of a fiber optic hydrogen sensor 400. In this example, a chromogenic hydrogen sensor is implemented. Exemplary hydrogen sensor 400 includes a sensor head 410 on a fiber optic cable 420, connected to a display 430 for outputting the hydrogen concentrations detected at the sensor head 410. Light from an electro-optic control unit (e.g., provided in housing 405) may be projected down the optical fiber 420 where it is either reflected by the sensor head 410 or is transmitted to another fiber leading to a remote optical detector (e.g., provided in housing 405). A change in the reflected or transmitted light intensity indicates the presence of hydrogen. Accordingly, hydrogen sensors such as these may be implemented to detect the presence of small quantities of hydrogen in the surrounding environment.

Figure 4A:
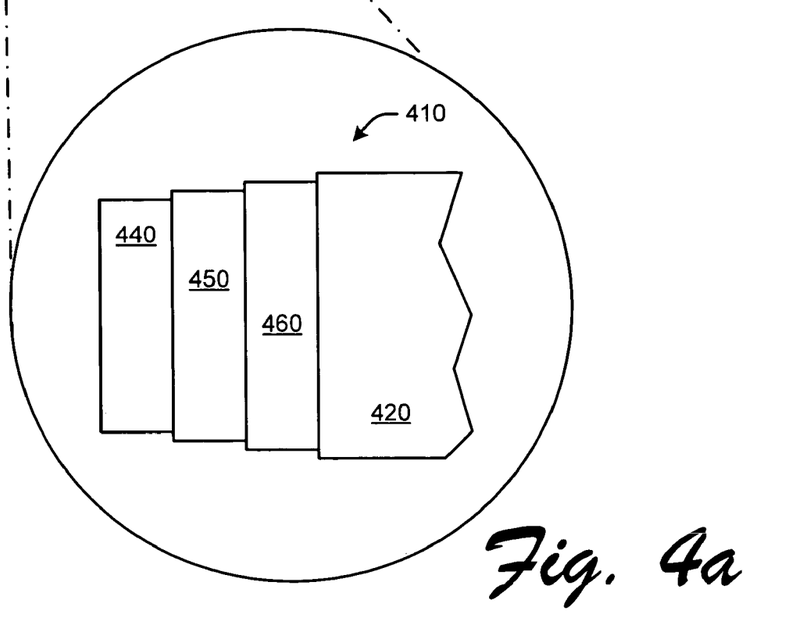
FIG. 4a is a detailed view of the sensor head shown in FIG. 4.

FIG. 4a is a detailed view of the sensor head 410 shown in FIG. 4. The sensor head 410 operates based on intercalation of atomic hydrogen into chromogenic material 460 to effect an optical change. This is accomplished by providing a surface film 450 that acts as a hydrogen dissociation catalyst (which separates the hydrogen molecule and rapidly transports atomic hydrogen to the indicator layers below). The most commonly used catalytic layers are Pd and Pd alloys, primarily alloys containing Ni, Cu or Ag. Fabrication of the sensor film uses a substrate 420 of glass or polymer, coated with a thin film of a chromogenic transition metal oxide compound (e.g., tungsten oxide, $WO_3$), which is subsequently over-coated with the catalyst layer (e.g., Pd). The optical state of the thin film stack is then probed by a light beam, which can be delivered from a remote source (e.g., sensor housing 405) by using either collimated radiation or fiber-optic cables (e.g., cable 420). A beam of light is passed through the chromogenic layer, and light intensity modulations in either transmission or reflection measurements indicate the presence of hydrogen.

Chromogenic sensors as described above provide sensitive detection of hydrogen in air, having the potential to provide inexpensive, reliable, and inherently safe hydrogen detectors. However, the lifetime of such sensors in air is limited (depending upon the quality of the surrounding air) and may function only a few days before serious degradation in sensor performance occurs.

Accordingly, a photo-oxidation catalyst, such as anatase $TiO_2$, may be implemented as a protective coating 440. When exposed to near ultraviolet (UV) light, the protective coating 440 served to clean the contaminated metal catalyst surfaces and to maintain them in an operational state. It has been shown that low levels of ultraviolet energy (approximately 7 $\mu W/cm^2$) are sufficient to maintain cleanliness of the surfaces.

In this example, a protective coating 440 of a colloidal suspension of anatase $TiO_2$ nanoparticles was synthesized by a hydrothermal process from an alkoxide precursor such as titanium isopropoxide [$Ti(C_3H_7O)_4$]. The particle size was in the range of 15-30 nm. The $TiO_2$ suspension was diluted in a solvent such as ethanol ($C_2H_5OH$) in a ratio optimized to obtain the proper consistency for coating. The coating was then spin-coated.

The semiconductor band gap of anatase $TiO_2$ is at 3.1 electron volts (eV), which corresponds to an adsorption maximum of about 390 nm. Therefore, the Pd catalyst with the $TiO_2$ coating was continuously exposed to UV radiation at 365 nm from a near UV source. The UV caused the $TiO_2$ particle surfaces to form hydroxide radicals from water vapor in the atmosphere. The radicals oxidized contaminants that were adsorbed on the $TiO_2$ surface. Additional radicals may also migrate from the $TiO_2$ to the metal surface. Contaminants that diffused through the coating and occupied sites on the metal surface may also be oxidized, converted to a volatile species and escape from the film. Both physisorbed and chemisorbed species were effectively removed.

Figure 5:
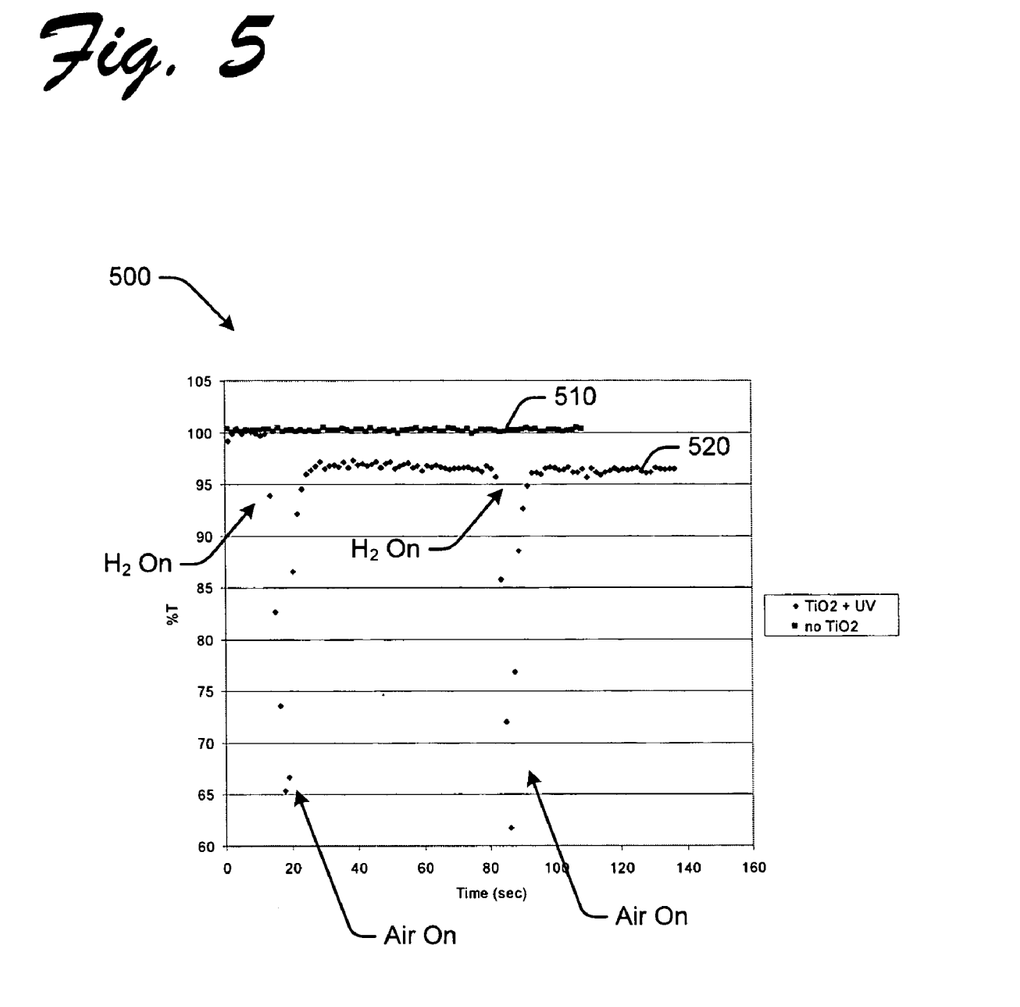
FIG. 5 is a plot showing the optical response of both an unprotected fiber optic hydrogen sensor, and a fiber optic hydrogen sensor protected by a photo-oxidation catalyst.

FIG. 5 is a plot 500 showing the optical response of both an unprotected fiber optic hydrogen sensor 510, and a fiber optic hydrogen sensor protected by a photo-oxidation catalyst 520 (e.g., the sensor described above with reference to FIGS. 4 and 4a). The fiber optic hydrogen sensors were exposed to 0.1% hydrogen gas after being exposed to ambient air for 10 days. It is observed that although the unprotected fiber optic hydrogen sensor was unable to detect the presence of hydrogen, the hydrogen sensor protected by a photo-oxidation catalyst remained sensitive to low concentrations of hydrogen (e.g., one tenth of one percent). In addition the hydrogen sensor protected by a photo-oxidation catalyst responded to the presence of the hydrogen molecules transported to the tungsten oxide within short time periods (e.g., one second). Moreover, the hydrogen sensor protected by a photo-oxidation catalyst detected the presence of hydrogen molecules at concentrations well below the explosive limit of four percent.

Figure 6:
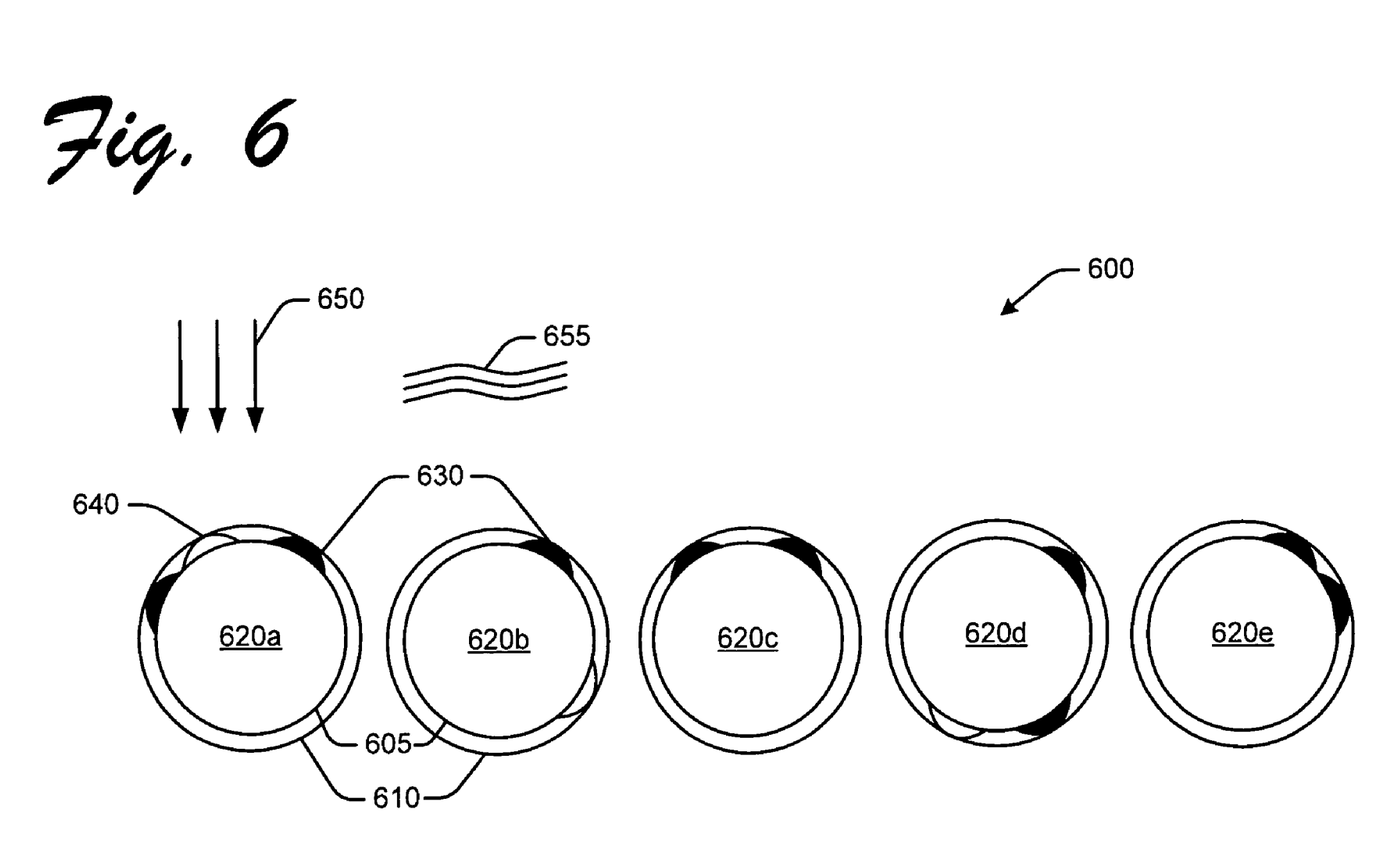
FIG. 6 is a high-level diagram of an exemplary catalyst bed protected by a photo-oxidation catalyst.

FIG. 6 is a high-level diagram of an exemplary catalyst bed 600 protected by a photo-oxidation catalyst 610. The photocatalyst 610 may be applied to the reactive surface 605 of the catalyst bed 600 as a thin film or thick film of photocatalytic material, or may be a composite of fine particles adhered to the substrate and surrounding the catalysts (e.g., spheres 620a-e). Accordingly, photo-oxidation of surface contaminants (e.g., illustrated as shaded binding sites 630) may be implemented to regenerate the catalyst bed (e.g., illustrated by clean binding sites 640).

In this example, the photocatalyst 610, in the presence of visible or ultraviolet light 650 and water vapor 655 (e.g., in the ambient air), "regenerates" or "cleans" contaminants from the reactive surface 605 of the catalyst bed 600. For example, binding sites with absorbed pollutants are regenerated or "cleaned."

It is noted that the examples discussed above are provided for purposes of illustration and are not intended to be limiting. Still other embodiments and modifications are also contemplated.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A catalyst system comprising:
   a substrate;
   a solid thin film metal-based catalyst on the substrate;
   a photo-oxidation catalyst on the outer surface of the metal-based catalyst so that the metal-based catalyst is situated between the substrate and the photo-oxidation catalyst, and the photo-oxidation catalyst is exposed to atmosphere for cleaning the metal-based catalyst in the presence of light, the exposure to light enabling the photo-oxidation catalyst to substantially oxidize absorbed contaminants from the atmosphere and reduce accumulation of the contaminants on the metal-based catalyst.

2. The catalyst system of claim 1, wherein the metal-based catalyst is selected from a group of noble and semi-noble metals comprising palladium, platinum, other metals of the platinum-group, and alloys thereof.

3. The catalyst system of claim 1, wherein the photo-oxidation catalyst defines a lower surface portion; the metal-based catalyst defining an upper interfacing surface portion; and the upper interfacing surface portion of the metal-based catalyst abutting the lower surface portion of the photo-oxidation catalyst.

4. The catalyst system of claim 1, wherein the photo-oxidation catalyst is selected from a group comprising anatase titania, and other metal oxides having substantially similar chemical and physical characteristics as a titania-type photo-oxidation catalysts.

5. The catalyst system of claim 1, wherein the photo-oxidation catalyst is selected to substantially oxidize and reduce accumulation on the metal-based catalyst of the contaminants from a group of pollutants comprising hydrocarbons, carbon monoxide, hydrogen sulfide, and other sulfur bearing gases.

6. The catalyst system of claim 1, further comprising a remote radiation source positioned adjacent the photo-oxidation catalyst to emit the light.

7. The catalyst system of claim 1, further comprising a remote radiation source selected to emit the light from a region of the electromagnetic spectrum comprising near ultraviolet radiation and ultraviolet radiation.

8. The catalyst system of claim 1, further comprising a remote radiation source selected to emit the light in the visible light spectrum.

9. The catalyst system of claim 1, further comprising a light source operatively coupled to the photo-oxidation catalyst and metal-based catalyst, wherein the light output by the light source is focused on the metal-based catalyst and photo-oxidation catalyst.

10. The catalyst system of claim 9, wherein the light source is from a group of light probes and guides comprising a plurality of fluorescent lamps assembled to provide a beam output, fiber optics, and high intensity discharge lamps.

11. The catalyst system of claim 9, wherein the light source is solar radiation.

12. The catalyst system of claim 1, wherein the photo-oxidation catalyst and metal-based catalyst comprise thin films.

13. The catalyst system of claim 1, wherein the metal-based catalyst is selected from a group of variously, geometrically shaped, thin films comprising a continuous thin film-type, a discontinuous thin film, and an island-configured thin film, or dispersed particulates on a support.

14. The catalyst system of claim 1, wherein the metal-based catalyst comprises a continuous thin film.

15. The catalyst system of claim 1, wherein the photo-oxidation catalyst comprises anatase titania.

16. The catalyst system of claim 1, wherein the metal-based catalyst comprises palladium.

17. The catalyst system of claim 1, wherein the light comprises wavelengths from about 254 nanometers to about 385 nanometers.

18. The catalyst system of claim 1, wherein the light is collimated light.

19. The catalyst system of claim 1, wherein the photo-oxidation catalyst during the exposure to the light and the reaction with ambient air enables the photo-oxidation catalyst to generate hydroxide radicals from water vapor during the reaction; the generated hydroxide radicals substantially oxidizing, firstly, the absorbed contaminants, and secondly, any surviving contaminants that migrate through the photo-oxidation catalyst to the metal-based catalyst.

20. The catalyst system of claim 1, wherein the photo-oxidation catalyst and metal-based catalyst are used in a sensor.

21. The catalyst system of claim 20, wherein the sensor is selected from a group comprising hydrogen field effect transistor sensors, hydrogen thick film sensors, hydrogen thin film sensors, hydrogen fiber-optic sensors, and chromogenic hydrogen sensors.

22. The catalyst system of claim 20, wherein the sensor comprises a chromogenic hydrogen sensor.

23. The catalyst system of claim 22, wherein the chromogenic hydrogen sensor comprises a thin-film metal oxide disposed over a substrate; and wherein the metal oxide is over coated with palladium.

24. The catalyst system of claim 23, wherein the substrate comprises glass.

25. The catalyst system of claim 23, wherein the substrate comprises a polymer.

26. The catalyst system of claim 23, wherein the substrate comprises the end of a fiber-optic cable.

27. The catalyst system of claim 23, wherein the metal oxide is selected from a group comprising tungsten oxide, molybdenum oxide, nickel oxide, nickel hydroxide, vanadium oxide, ruthenium oxide, and suitably doped states of these oxides.

28. The catalyst system of claim 1, wherein the photo-oxidation catalyst and metal-based catalyst are used in the reactive surface of a catalyst bed.

29. A hydrogen sensor comprising:
   a composite of thin films, including:
      a coating of titanium dioxide defining a top thin film;
      a catalytic layer of palladium defining an intermediate thin film, the titanium dioxide thin film provided over the catalytic layer of palladium and exposed to atmosphere such that the titanium dioxide thin film reduces accumulation of contaminants from the atmosphere on the catalytic layer of palladium; and
      a chemochromic layer of tungsten oxide defining a bottom thin film;

a glass substrate supporting the composite of thin films; and a light source for probing the composite of thin films with light to facilitate a reaction with the ambient air and water vapor therein, causing photo-oxidation of contaminants on the composite of thin films.

30. The hydrogen sensor of claim 29, wherein the light source is an ultraviolet light source.

31. The hydrogen sensor of claim 29, wherein the oxidation of contaminants enables the hydrogen sensor to be operational for at least a period of one year during repeated exposures to hydrogen.

32. A method for cleaning a metal-based catalyst, comprising:

providing a substrate and a photo-oxidation catalyst adjacent the metal-based catalyst such that the substrate is positioned on one surface of the metal-based catalyst and the photo-oxidation catalyst is positioned on an opposite surface of the metal-based catalyst and exposed to atmosphere to reduce accumulation of contaminants from the atmosphere on the metal-based catalyst; and exposing the photo-oxidation catalyst to light to oxidize absorbed contaminants on the metal-based catalyst thus cleaning and restoring to service a previously fouled metal catalyst surface.

33. The method of claim 32, wherein the light is ultraviolet light.

34. The method of claim 32, wherein the metal-based catalyst is selected from a group of noble and semi-noble metals comprising palladium, platinum, other metals of the platinum-group, and alloys thereof.

35. The catalyst system of claim 32, wherein the photo-oxidation catalyst is selected from a group comprising anatase titania, and other metal oxides having substantially similar chemical and physical characteristics as a titania-type photo-oxidation catalysts.

36. A hydrogen sensor with contaminant cleaning system comprising:

a substrate;

a solid thin film palladium catalyst;

a titanium dioxide photo-oxidation catalyst provided on the outer surface of the palladium catalyst during assembly at room temperature, the palladium catalyst positioned between the substrate and the titanium dioxide photo-oxidation catalyst, the titanium dioxide photo-oxidation catalyst exposed to atmosphere for cleaning the palladium catalyst in the presence of light, the exposure to light enabling the titanium dioxide photo-oxidation catalyst to substantially oxidize absorbed contaminants from the atmosphere and reduce accumulation of the contaminants on the palladium catalyst.

* * * * *